(12) United States Patent
Eddy

(10) Patent No.: US 9,028,846 B2
(45) Date of Patent: May 12, 2015

(54) BEDS AND BED ACCESSORIES HAVING AN ANTIMICROBIAL TREATMENT

(75) Inventor: Patrick E. Eddy, Allendale, MI (US)

(73) Assignee: Parasol Medical LLC, Buffalo Grove, IL (US)

( * ) Notice: Subject to any disclaimer, the term of this patent is extended or adjusted under 35 U.S.C. 154(b) by 0 days.

(21) Appl. No.: 13/448,798

(22) Filed: Apr. 17, 2012

(65) Prior Publication Data

US 2013/0273133 A1    Oct. 17, 2013

(51) Int. Cl.
| | |
|---|---|
| *A61K 9/00* | (2006.01) |
| *A01N 33/12* | (2006.01) |
| *A61K 47/48* | (2006.01) |
| *A01N 55/00* | (2006.01) |
| *A61M 25/00* | (2006.01) |

(52) U.S. Cl.
CPC .......... *A01N 33/12* (2013.01); *A61K 47/48115* (2013.01); *A61K 2800/57* (2013.01); *A61M 2025/0056* (2013.01); *A01N 55/00* (2013.01)

(58) Field of Classification Search
CPC ................................ A01N 25/34; A47C 19/02
See application file for complete search history.

(56) References Cited

U.S. PATENT DOCUMENTS

| | | | |
|---|---|---|---|
| 5,079,004 A | 1/1992 | Blank et al. | |
| 5,428,078 A | 6/1995 | Cohen et al. | |
| 5,959,014 A | 9/1999 | Liebeskind et al. | |
| 6,224,579 B1 | 5/2001 | Modak et al. | |
| 7,045,673 B1 | 5/2006 | Batich et al. | |
| 7,709,694 B2 | 5/2010 | Batich et al. | |
| 7,790,217 B2 | 9/2010 | Toreki et al. | |
| 8,025,120 B2 | 9/2011 | Eddy | |
| 8,491,922 B2 | 7/2013 | Eddy | |
| 2003/0073600 A1* | 4/2003 | Avery et al. ................... | 510/382 |
| 2007/0042198 A1 | 2/2007 | Schonemyr et al. | |
| 2007/0218096 A1 | 9/2007 | Wooley | |
| 2008/0260804 A1 | 10/2008 | Morris et al. | |
| 2012/0173274 A1* | 7/2012 | Rensvold et al. ................. | 705/2 |

FOREIGN PATENT DOCUMENTS

WO        2008097599 A2      8/2008

OTHER PUBLICATIONS

Proguard Quaternary Disinfectant (http://www.kellysolutions.com/wa/showAl.asp?Basic_EPA_ID=6836%2D78&EPA_ID=6836%2D78%2D1677&Product_Name=Quaternary+Disinfectant+Cleaner+ProGuard (downloaded on Jun. 26, 2013)).*
Murray et al., "Microbial Inhibition on Hospital Garments Treated with Dow Corning 5700 Antimicrobial Agent," Journal of Clinical Microbiology, vol. 26, No. 9, Sep. 1988, pp. 1884-1886.

* cited by examiner

*Primary Examiner* — Paul Dickinson
(74) *Attorney, Agent, or Firm* — Price Heneveld LLP

(57) ABSTRACT

A hospital bed is provided that may include a support structure having a plurality of surfaces coated with an antimicrobial treatment, which may include a silane quaternary ammonium salt and isopropyl alcohol. The silane quaternary ammonium salt may include an unreacted organofunctional silane to promote bonding to the surfaces of the bed, such as 3-(trimethoxysilyl) propyldimethyloctadecyl ammonium chloride. Bed accessories, such as tables and IV stands, may also include the antimicrobial treatment. A method is also provided for coating these articles with the antimicrobial treatment.

17 Claims, 4 Drawing Sheets

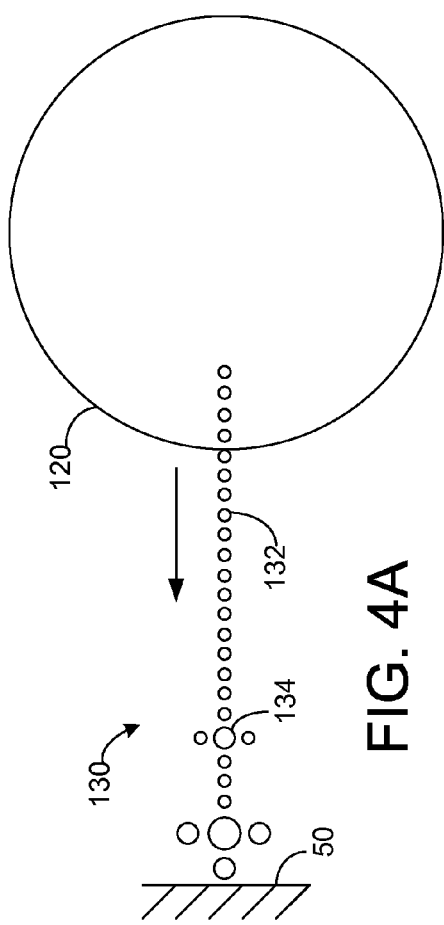
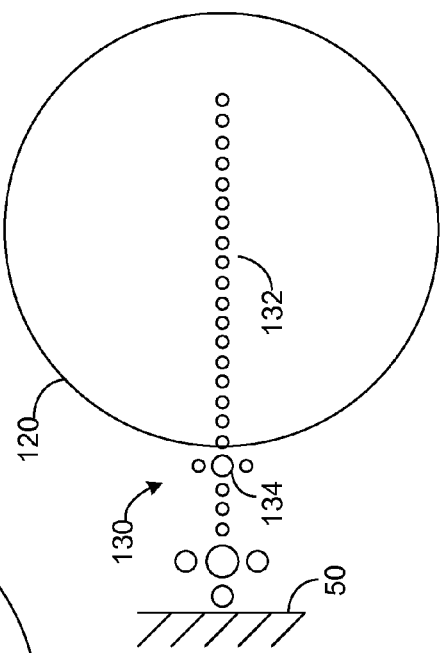
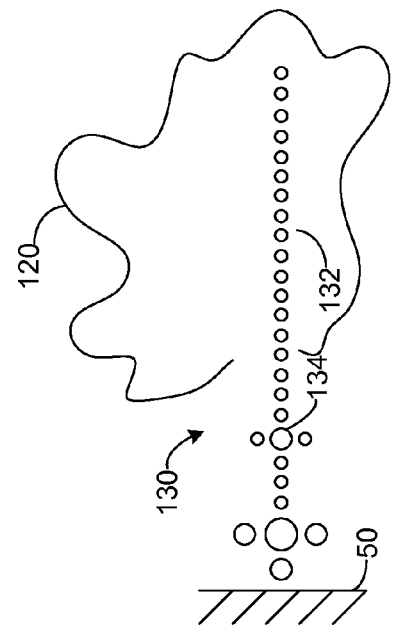

BEDS AND BED ACCESSORIES HAVING AN ANTIMICROBIAL TREATMENT

BACKGROUND OF THE INVENTION

The present invention generally relates to beds and bed accessories, and more particularly relates to beds and bed accessories of the type used in healthcare facilities, such as hospitals, hospices, nursing homes, assisted living homes, etc.

Hospitals continue to struggle to prevent dangerous infections caused by bacteria such as MRSA, and others. Although hospital staff frequently change sheets on beds and wipe down the bed with disinfectants, the beds are often found to still carry dangerous bacteria.

SUMMARY OF THE INVENTION

According to an embodiment of the present invention, a bed is provided comprising a support structure having a plurality of surfaces coated with an antimicrobial treatment comprising a silane quaternary ammonium salt.

According to another embodiment of the present invention, a method is provided for treating a bed with an antimicrobial treatment solution comprising the steps of: providing an antimicrobial treatment solution comprising isopropyl alcohol and an antimicrobial treatment substance, wherein the antimicrobial treatment substance may comprise a silane quaternary ammonium salt; and applying the antimicrobial treatment solution to surfaces of the bed support structure.

According to another embodiment of the present invention, a bed accessory is provided comprising a structure having a plurality of surfaces coated with an antimicrobial treatment comprising a silane quaternary ammonium salt.

In one or more of these embodiments, the silane quaternary ammonium salt may have an unreacted organofunctional silane to promote bonding to the surfaces of the bed. The silane quaternary ammonium salt may comprise 3-(trimethoxysilyl) propyldimethyloctadecyl ammonium chloride.

These and other features, advantages, and objects of the present invention will be further understood and appreciated by those skilled in the art by reference to the following specification, claims, and appended drawings.

BRIEF DESCRIPTION OF THE DRAWINGS

In the drawings:

FIG. 4A is a schematic representation of the monomer shown in FIGS. 2 and 3 illustrating a first step in the manner by which the monomer destroys a microbe;

FIG. 4B is a schematic representation of the monomer shown in FIGS. 2 and 3 illustrating a second step in the manner by which the monomer destroys a microbe; and FIG. 4C is a schematic representation of the monomer shown in FIGS. 2 and 3 illustrating a third step in the manner by which the monomer destroys a microbe.

DETAILED DESCRIPTION OF PREFERRED EMBODIMENTS

Figure 1:
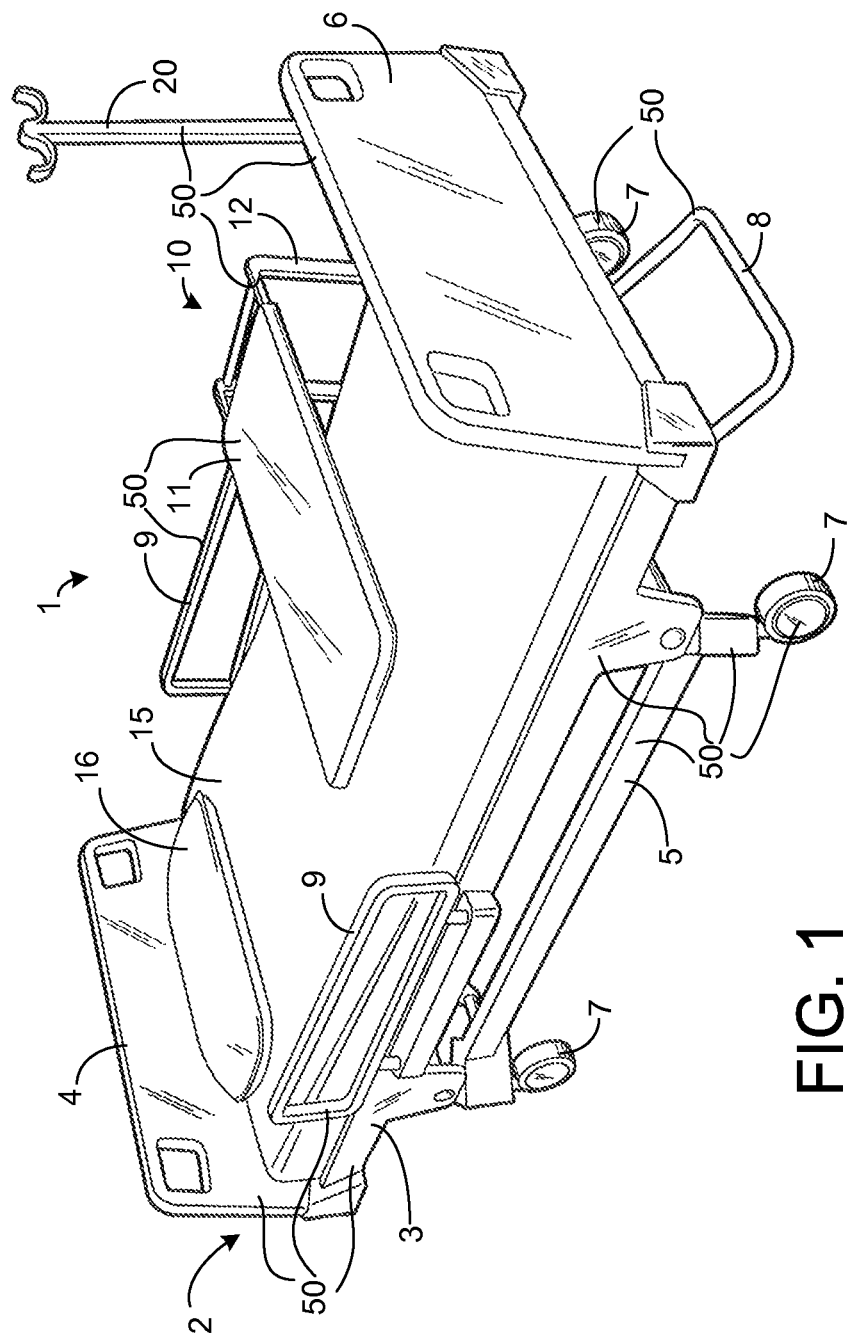
FIG. 1 is a perspective view of a bed, table, and IV stand treated in accordance with an embodiment of the present invention.

Reference will now be made in detail to the present preferred embodiments of the invention, examples of which are illustrated in the accompanying drawings. Wherever possible, the same reference numerals will be used throughout the drawings to refer to the same or like parts. In the drawings, the depicted structural elements are not to scale and certain components are enlarged relative to the other components for purposes of emphasis and understanding.

FIG. 1 shows a novel hospital bed 1 having some or all of its surfaces 50 coated with an antimicrobial treatment. As shown, bed 1 may include a mattress 15 and a support structure 2. Support structure 2 may include: a frame assembly 3; a headboard 4; a base 5; a footboard 6; a plurality of wheels 7; a foot lever 8 for adjusting the bed; and a pair of rails 9. Frame assembly 3 is height-adjustable and supported on base 5, which, in turn, is supported by wheels 7. Frame assembly 3 supports mattress 15 and any pillows 16. Rails 9 are attached to the bed so as to be movable from a stowed position (not shown) to an upright position (as shown in FIG. 1) along and above mattress 15. The components of support structure 2 are often constructed of a variety of materials including vinyls, metals, laminates and a variety of plastics. Each of these components of support structure 2, as well as any other components not specifically mentioned herein, have outer surfaces 50, which are coated with the antimicrobial treatment as described further below. Preferably all surfaces 50 of the components of support structure 2 are treated.

The surfaces 50 are coated with an antimicrobial treatment that may be sprayed onto the surfaces using a solution and/or may be applied using wipes soaked in such a solution. Suitable wipes and solutions are disclosed in commonly-assigned U.S. patent application Ser. No. 13/182,657, entitled "ANTIMICROBIAL WIPES AND SOLUTION," filed on Jul. 14, 2011, by Patrick E. Eddy, the entire disclosure of which is incorporated herein by reference.

Bed accessories may also be treated with such an antimicrobial treatment solution. As also described herein, a "bed accessory" includes but is not limited to, associated tables 10, IV stands 20, and control buttons and panels for operating the bed or other accessories. Such accessories typically comprise a structure having a plurality of surfaces that may be treated. For example, as shown in FIG. 1, table 10 includes a table top 11 and support members 12, which may all be treated with the antimicrobial treatment.

In a preferred form, the antimicrobial treatment solution contains 30-50 percent isopropyl alcohol and 50-70 percent antimicrobial treatment substance, which is preferably a silane quaternary ammonium salt having an unreacted organofunctional silane. If the antimicrobial treatment solution is applied by spraying, the solution most preferably includes 50 percent isopropyl alcohol and 50 percent of the unreacted antimicrobial treatment substance. If the solution is applied using the wipes, the solution is preferably 30 percent isopropyl alcohol and 70 percent of the unreacted antimicrobial treatment substance.

The preferred silane quaternary ammonium salt includes an active ingredient of 3-(trimethoxysilyl) propyldimethyloctadecyl ammonium chloride and other inert ingredients. The silane quaternary ammonium salt preferably includes about 3.6 percent of the 3-(trimethoxysilyl) propyldimethyloctadecyl ammonium chloride. Such a silane quaternary ammonium salt is available from Aegis Environments, of Midland, Michigan, and is identified as "AEM 5772-5 Antimicrobial." The antimicrobial treatment solution with the isopropyl alcohol is available from MicrobeCare, LLC of Allendale, Michigan, under the trademark MICROBECARE™.

The isopropyl alcohol may have a concentration of 70-90 percent. By providing the unreacted organofunctional silane in isopropyl alcohol, the organofunctional silane does not react with the wipe substrates or the inside of the wipe container such that it is free to later react and permanently covalently bond with the surfaces 50 of bed 1. Isopropyl alcohol is preferred as it evaporates quickly once the solution is wiped onto the treated surface to allow the unreacted organofunctional silane to more quickly react with the treated surface.

The above described silane quaternary ammonium salt is preferred because it is an organofunctional silane antimicrobial treatment substance that is substantially free from arsenic, silver, tin, heavy metals and polychlorinated phenols; copper; or a silver-ion emitter. In addition, it not only eliminates bacteria on contact, but it remains on the treated bed surfaces 50 and kills any bacteria subsequently contacting these surfaces. Such treatment preferably lasts at least one week, more preferably several months, and most preferably indefinitely.

Figure 2:
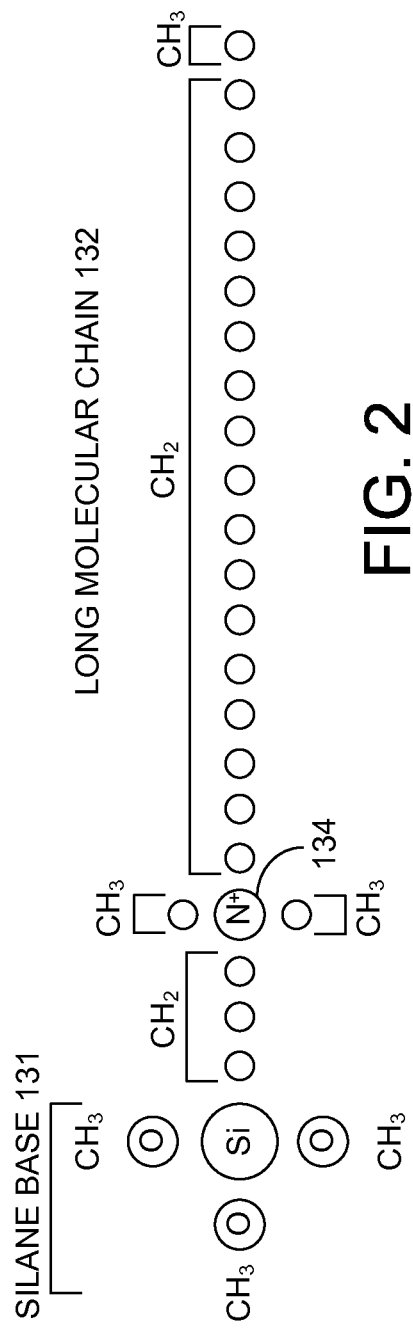
FIG. 2 is a schematic representation of a monomer that may be used in the embodiments described herein as an antimicrobial treatment substance.
Figure 3:
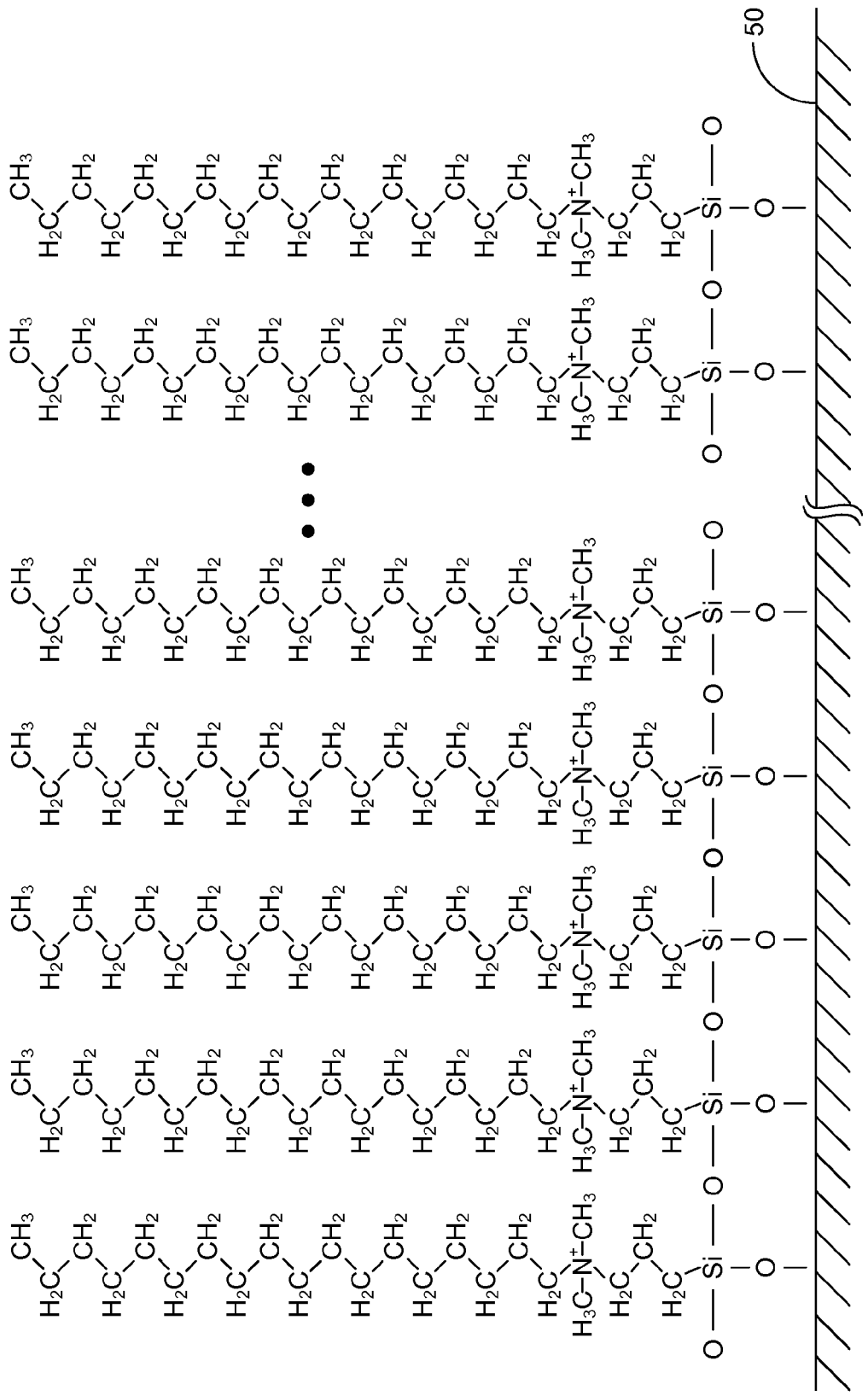
FIG. 3 is a schematic representation of a plurality of the monomers shown in FIG. 2 as applied to a treated surface.

FIG. 2 shows a schematic representation of a monomer form 130 of a preferred organofunctional silane serving as the antimicrobial treatment substance. As illustrated, monomer 130 includes a silane base 131 for bonding to a surface 50, a positively charged nitrogen molecule 134, and a long molecular chain 132. As shown in FIG. 3, the silane bases of these monomers covalently and permanently bond to each other and to the surface 50 to be treated in such a way that the long molecular chains are aligned and pointing outward from the surface 50. This tight bonding provides a micropolymer network that serves as a protective coating on the outside of the surface 50 that destroys any microbes that come into contact.

The manner by which the preferred organofunctional silane destroys microbes is illustrated in FIGS. 4A-4C. Such microbes may include bacteria, mold, mildew, algae, etc. As shown in FIG. 4A, the cell membrane 120 of the microbe is attracted to the treated surface 50 of bed 1 and then is punctured by the long molecular chain 132 of the monomer 130. As the microbe is drawn closer because of the positive-negative ion exchange, the monomer 130 penetrates further into the cell membrane 120 as shown in FIG. 4B. Once the cell membrane 120 is penetrated deeply, it is physically ruptured by a sword-like action and then electrocuted by a positively charged nitrogen molecule 134 of the monomer 130, thus destroying the microbe as illustrated in FIG. 4C. Thus, the microbes are eliminated without "using up" any of the antimicrobial active ingredients, which remain on the surfaces 50 ready to continue protecting the treated item against further microbial contamination.

The preferred organofunctional silane also prevents odor, staining and product deterioration that may be associated with microbe contamination. The preferred organofunctional silane is also beneficial because it permanently bonds to a treated surface, covers a broad spectrum of activity with no negative effects or drawbacks and is easily incorporated and easily verifiable.

The preferred organofunctional silane is designed to react and create a covalent bond with the surfaces 50 of bed 1. The reacted substance is held onto those surfaces 50 until the covalent bond is broken. Tests have shown that most industrial cleaners or disinfectants will not remove the preferred antimicrobial treatment substance. The method of removal is by abrasion.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the claims as interpreted according to the principles of patent law, including the doctrine of equivalents.

I claim:

1. A bed comprising:
a support structure having a plurality of surfaces coated with an antimicrobial treatment,
wherein said antimicrobial treatment comprises a silane quaternary ammonium salt including an unreacted organofunctional silane to promote covalent bonding to the surfaces of the bed, wherein the antimicrobial treatment is covalently bonded to the surfaces and is capable of emitting ions that aid in the destruction of a microbe.

2. The bed of claim 1, wherein said silane quaternary ammonium salt comprises 3-(trimethoxysilyl) propyldimethyloctadecyl ammonium chloride.

3. The bed of claim 1, wherein said antimicrobial treatment comprises an antimicrobial treatment solution comprising isopropyl alcohol and an antimicrobial treatment substance including said silane quaternary ammonium salt.

4. The bed of claim 3, wherein the antimicrobial treatment solution comprises about 30 percent to about 50 percent of isopropyl alcohol.

5. The bed of claim 3, wherein the antimicrobial treatment solution comprises about 50 percent to about 70 percent of the antimicrobial treatment substance.

6. The bed of claim 1, wherein said antimicrobial treatment is free from arsenic, silver, tin, heavy metals and polychlorinated phenols.

7. The bed of claim 1, wherein said support structure includes at least one of: a frame assembly; a base; a headboard; a footboard; a plurality of wheels; a foot lever; and a pair of rails.

8. A bed accessory comprising:
a structure having a plurality of surfaces coated with an antimicrobial treatment,
wherein said antimicrobial treatment comprises a silane quaternary ammonium salt, wherein said silane quaternary ammonium salt includes an unreacted organofunctional silane to promote bonding to the surfaces of the bed by forming covalent bonds to the surfaces.

9. The bed accessory of claim 8, wherein said bed accessory comprises a table.

10. The bed accessory of claim 8, wherein said bed accessory comprises an IV stand.

11. The bed accessory of claim 8, wherein said silane quaternary ammonium salt comprises 3-(trimethoxysilyl) propyldimethyloctadecyl ammonium chloride.

12. The bed accessory of claim 8, wherein said antimicrobial treatment comprises an antimicrobial treatment solution comprising said silane quaternary ammonium salt and isopropyl alcohol.

13. The bed accessory of claim 12, wherein the antimicrobial treatment solution comprises about 30 percent to about 50 percent of isopropyl alcohol.

14. The bed accessory of claim 12, wherein the antimicrobial treatment solution comprises about 50 percent to about 70 percent of silane quaternary ammonium salt.

15. The bed accessory of claim 8, wherein the antimicrobial treatment solution comprises about 50 percent to about 70 percent of the silane quaternary ammonium salt.

16. The bed of claim 1, wherein the antimicrobial treatment solution comprises about 50 percent to about 70 percent of the silane quaternary ammonium salt.

17. The bed of claim 16, wherein said silane quaternary ammonium salt comprises 3-(trimethoxysilyl) propyldimethyloctadecyl ammonium chloride.

* * * * *